United States Patent
Levey et al.

(10) Patent No.: US 12,324,675 B2
(45) Date of Patent: Jun. 10, 2025

(54) SYSTEMS AND METHODS FOR AUTOMATED PASSIVE ASSESSMENT OF VISUOSPATIAL MEMORY AND/OR SALIENCE

(71) Applicant: EMORY UNIVERSITY, Atlanta, GA (US)

(72) Inventors: Allan Levey, Atlanta, GA (US); Gari Clifford, Atlanta, GA (US); Rafi Haque, Atlanta, GA (US); Cecelia Manzanares, Atlanta, GA (US); LaVonda Brown, Atlanta, GA (US)

(73) Assignee: Emory University, Atlanta, GA (US)

( * ) Notice: Subject to any disclaimer, the term of this patent is extended or adjusted under 35 U.S.C. 154(b) by 1088 days.

(21) Appl. No.: 17/286,667

(22) PCT Filed: Oct. 21, 2019

(86) PCT No.: PCT/US2019/057277
§ 371 (c)(1),
(2) Date: Apr. 19, 2021

(87) PCT Pub. No.: WO2020/082088
PCT Pub. Date: Apr. 23, 2020

(65) Prior Publication Data
US 2021/0353208 A1  Nov. 18, 2021

Related U.S. Application Data

(60) Provisional application No. 62/747,682, filed on Oct. 19, 2018.

(51) Int. Cl.
*A61B 5/00* (2006.01)
*A61B 5/16* (2006.01)

(52) U.S. Cl.
CPC ............ *A61B 5/4088* (2013.01); *A61B 5/163* (2017.08); *A61B 5/165* (2013.01); *A61B 5/7275* (2013.01)

(58) Field of Classification Search
CPC ....... A61B 5/163; A61B 5/165; A61B 5/4088; A61B 5/1103; A61B 5/7264;
(Continued)

(56) References Cited

U.S. PATENT DOCUMENTS

2012/0059282 A1  3/2012  Agichtein et al.
2013/0090562 A1  4/2013  Ryan
(Continued)

FOREIGN PATENT DOCUMENTS

WO   2017/171655 A1   10/2017

OTHER PUBLICATIONS

Haque et al, "VisMET: a passive, efficient, and sensitive assessment of visuospatial memory in healthy aging, mild cognitive impairment, and Alzheimer's disease", Learning & Memory, vol. 26, No. 3, Mar. 1, 2019, pp. 93-100.

(Continued)

*Primary Examiner* — Brandi N Thomas
(74) *Attorney, Agent, or Firm* — Meunier Carlin & Curfman LLC

(57) ABSTRACT

Techniques are provided for determining a qualitative, quantitative and/or categorical assessment of one or more users and/or images with respect to one or more populations. The eye movement data of the user may be obtained with respect to each image of the one or more images displayed for a period of time. One or more memory performance measures and/or one or more salience performance measures may be determined using the eye movement data with respect to the one or more regions of the one or more images for one or more of predetermined time ranges of the period of time.

(Continued)

The quantitative, qualitative and/or categorical assessment of the user and/or images presented may be determined with respect to one or more populations, using the one or more memory performance measures and/or one or more salience performance measures.

16 Claims, 7 Drawing Sheets

(58) Field of Classification Search
CPC ... A61B 5/7275; A61B 5/7445; A61B 5/7475; A61B 3/113; G06V 40/193; G06V 20/59; G06V 40/166; G06V 40/165; G06V 40/19; G06V 20/46; G06V 40/161; G06V 40/162; G06V 40/171; G06V 40/197; G06F 3/013; G06F 2203/011; G06F 3/012; G06F 3/0346; G06F 3/14; G06F 3/1454; G06F 3/005
See application file for complete search history.

(56) References Cited

U.S. PATENT DOCUMENTS

| | | |
|---|---|---|
| 2015/0282705 A1 | 10/2015 | Avital |
| 2015/0338915 A1* | 11/2015 | Publicover .......... H04W 12/065 345/633 |
| 2017/0135577 A1 | 5/2017 | Komogortsev |

OTHER PUBLICATIONS

Extended European Search Report issued in EP 19873849.4, mailed Jun. 28, 2022.

International Search Report and Written Opinion for International Application No. PCT/US2019/0557277 dated Dec. 31, 2019.

Freitas Pereira, Eye movement analysis and cognitive processing: detecting indicators of conversion to Alzheimer's disease, Neuropsychiatric Disease and Treatment, Jul. 9, 2014, vol. 10, pp. 1273-1285.

Written Opinion and Search Report issued in SG 112021034385, mailed Dec. 12, 2022.

* cited by examiner

SYSTEMS AND METHODS FOR AUTOMATED PASSIVE ASSESSMENT OF VISUOSPATIAL MEMORY AND/OR SALIENCE

CROSS-REFERENCE TO RELATED APPLICATIONS

This application is a national stage application filed under 35 U.S.C. § 371 of PCT/US2019/057277 filed Oct. 21, 2019, which claims the benefit of U.S. Provisional Application No. 62/747,682 filed Oct. 19, 2018. The entirety of these applications are hereby incorporated by reference for all purposes.

BACKGROUND

Pathological changes in cognitive disorders, such as Alzheimer's disease (AD), can develop years before the onset of clinical symptoms. Memory paradigms, such as Rey Auditory Verbal Learning Test and Benton Visual Retention Test, have been used to detect AD during its early stages. However, these memory tests cannot reliably detect memory impairment early in the disease course. These tests also generally require significant resources, such as trained personnel to administer the test in a clinical setting and a considerable amount of time to administer. Participants also do not like the testing due to poor perceived performance on such tests. As a result, these tests are often underused. A critical need exists to develop an easily administered, sensitive, and non-threatening memory paradigm that can track memory performance through the different stages of memory loss as they occur in healthy aging and Alzheimer's disease.

SUMMARY

Thus, there is a need for accurate and efficient assessment that can detect and/or track memory performance as well as salience performance.

The systems and methods of the disclosure can provide a passive, efficient, and sensitive assessment that can detect memory and salience performance. The systems and methods can transform estimations of gaze of a user detected by an eye tracker into measures of visuospatial salience and/or memory based on viewing of different images. These measures can be used for a qualitative, quantitative and/or categorical assessment of one or more users and/or images with respect to one or more populations (e.g., individuals diagnosed with Alzheimer's disease).

In some embodiments, a method may be provided that determines a qualitative, quantitative and/or categorical assessment of one or more users and/or images with respect to one or more populations. The method may include presenting a test to a user on a display screen of a computing device. The test may include displaying one or more images from a first collection and/or a second collection for a period of time, each image of each collection including one or more regions. The method may further include obtaining eye movement data of the user with respect to each image of the one or more images displayed. The eye movement data for each image may include eye gaze position data for the period of time. The method may further include determining one or more memory performance measures and/or one or more salience performance measures using the eye movement data with respect to the one or more regions of the one or more images for one or more of predetermined time ranges of the period of time. The method may further include determining a quantitative, qualitative and/or categorical assessment of the user with respect to one or more populations, using the one or more memory performance measures and/or one or more salience performance measures.

In some embodiments, a method may be provided for training a model for performing a qualitative, quantitative and/or categorical assessment of one or more users and/or images with respect to one or more populations. The method may include receiving eye movement data of a plurality of users with respect to each image of the one or more collections of images displayed, the eye movement data for each image including eye gaze position data for a period of time. The method may further include determining a first set of one or more memory performance measures and/or one or more salience performance measures using the eye movement data with respect to the one or more regions of the one or more images for a plurality of time ranges of the period of time. The method may include determining a second set of one or more memory performance measures and/or one or more salience performance measures using the first set of one or more memory performance values and/or one or more salience performance measures for a predetermined time range of the plurality of time ranges.

In some embodiments, the method may include assessing the one or more collections of images using the second set of one or more memory performance measures and/or one or more salience performance measures.

In some embodiments, the method may include determining a third set of one or more memory performance measures and/or one or more salience performance measures using the second set of one or more memory performance measures and/or one or more salience performance measures and a difference between each respective performance measure. In some embodiments, the method may further include determining one or more parameters for a test to assess an individual with respect to one or more populations, the one or more parameters including the one or more images of the first collection and/or the second collection to include in the test and the predetermined time range for each image for which the one or more performance measures is determined; and generating at least one test using the one or more parameters.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, the emphasis being placed upon illustrating the principles of the disclosure.

DESCRIPTION OF THE EMBODIMENTS

Figure 1:
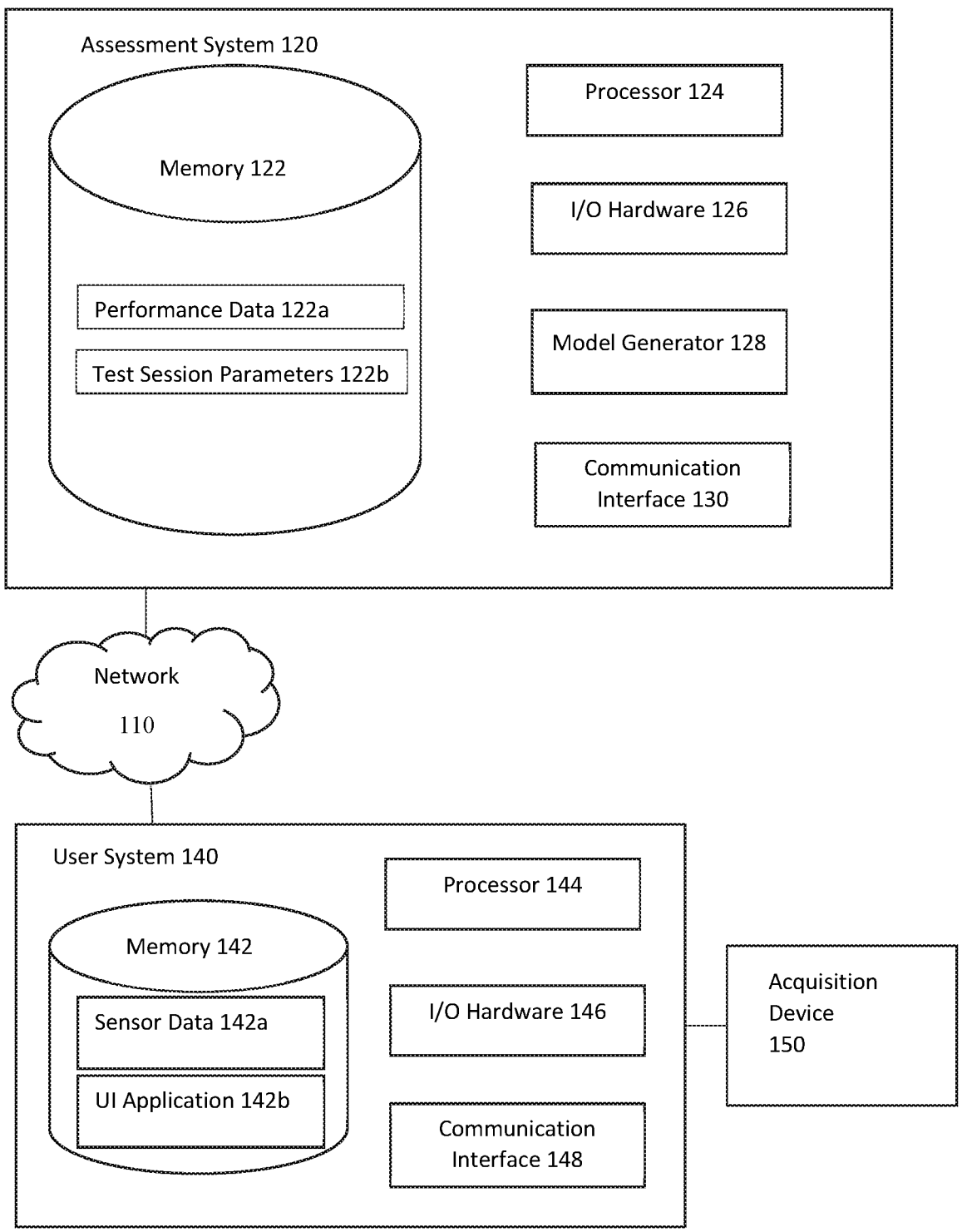
FIG. 1 shows a block diagram illustrating an example of a system according to embodiments.

In the following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

The disclosure relates to systems and methods that determine a quantitative, qualitative and/or categorical assessment of a user and/or images using one or more salience or memory performance measures. For example, the systems and methods can use these measures to distinguish the different stages of a cognitive disorder (e.g., AD), impairment, aging, among others. By way of another example, the systems and methods can use these measures to distinguish saliency of one or more images (e.g., content) with respect to different populations (e.g., old vs. young). The systems and methods can determine these measures without the need of significant resources, such as trained personnel and/or clinical resources. For example, the assessment test to determine these measures for the assessment may be administered using a tablet and/or a personal computer having a camera. A "user" can refer to a patient and/or individual user or subject for which the salience and/or memory measure assessment is being performed for determination of one or more testing parameters (e.g., training the model), assessment of the individual user, and/or assessment of the image(s) with respect to the user population.

While some examples of the disclosure may be specific to qualitative, quantitative, and/or categorical assessment of a cognitive disorder (e.g., Alzheimer's disease), it will be understood that these examples are nonlimiting and that the methods and systems may be used to assess within any one population, any two or more populations, among others, or any combination thereof. By way of example, the methods and systems of the disclosure may be configured to assess a user with respect to one or more populations with respect to demographical information (e.g., gender, race, age, etc.), aa condition or disease (e.g., cognitive disorder (e.g., Alzheimer's Disease, mild cognitive impairment, dementia, etc.), neurological disorder, brain injury (e.g., concussion), etc.), among others, or a combination thereof. For example, the systems and methods may determine a probability representing a likelihood of whether a user has a disorder or not, a user is at risk for that disorder, among others, or a combination thereof. In this example, the one or more populations may include users that have that condition and users that are healthy. This probability may represent the quantitative, qualitative and/or categorical assessment.

Additionally, while some examples of the disclosure may be specific to assessing a user, it will be understood that these examples are also nonlimiting and that embodiments of the methods and systems may also be applied to assess images with regards to the effectiveness of the content delivering the intended message to an intended audience, e.g., in drawing attention the intended audience to a particular element or elements of the content, such as an image, a color, a textual display, a design, a sound, a brand, among others, or any combination thereof; any arrangement thereof with respect to the image and/or display screen; among others; or any combination thereof.

In this description and in the claims, the term "computing system" or "computer architecture" is defined broadly as including any standalone or distributed device(s) and/or system(s) that include at least one physical and tangible processor, and a physical and tangible memory capable of having thereon computer-executable instructions that may be executed by the processor(s).

FIG. 1 illustrates an exemplary system 100 for a quantitative, qualitative, and/or categorical assessment of user(s) and/or image(s). In some embodiments, the system 100 may include an assessment system 120 (e.g., one or more cloud computing systems, one or more servers, one or more computers, one or more user devices, etc.) and a user system 140 (e.g., a computer, tablet, smart phone, or smart wearable), which may communicate to each other over a network 110 (e.g., the Internet, a local area network, a wide area network, a short-range network, a Bluetooth® network, etc.).

The system 100 may include one or more acquisition devices 150 may include one or more sensors for acquiring data of the user. For example, the one or more acquisition devices may include an eye tracking device (e.g., an image sensor (e.g., a camera such as an infrared eye tracking camera) capable of detecting and measure eye movement data (e.g., eye gaze position) of the user. By way of example, the eye tracker may be a hardware device and/or software used for monitoring the eye movements of user interacting with the system aimed at identifying a pupil position and/or gaze direction. For example, the eye tracker may include but is not limited to one more image sensors (cameras), depth sensors, infrared lighting sources, among others, or a combination thereof. By way of example, the eye tracking device may include a camera (optionally including an infrared-emitting light source) that is a part of a wearable computing device (e.g., glasses), that is a part of a tablet, that is a part of a computer, a separate device connected to the user system 140, among others, or a combination thereof.

In some embodiments, the eye movement data may include and is not limited to eye gaze location (e.g., coordinates with respect to the display screen) defined by time.

In some embodiments, the one or more acquisition devices 150 may include one or more additional (hardware and/or software-based) devices or sensors to acquire additional behavioral/sensory data and/or other physiological data of the user, such as an accelerometer, a gyroscope, a head-tracking sensor, a body temperature sensor, a heart rate sensor, a blood pressure sensor, a skin conductivity sensor, a microphone, among others, or a combination thereof.

The acquisition device(s) 150 may be configured to calibrate that data so that the data provided to the user system 140 and/or the assessment system 120 is calibrated. In some embodiments, the one or more acquisition devices 150 may be connected to the user system 140. In some embodiments, the acquisition device 150 can transmit the data (e.g., calibrated eye movement data) to the assessment device 120.

In some embodiments, the assessment system 120 may include a memory 122 and the user system 140 may include a memory 142. The memory 122 and 142 may independently be physical system memory, which may be volatile, non-volatile, or some combination of the two. The term "memory" may also be used herein to refer to non-volatile mass storage such as physical storage media. For example, the memory 122 and 142 may include random access memory (RAM), read-only memory (ROM), disk drive, etc., or any combinations thereof. The memory may be configured to store programs and data, including data structures. In some embodiments, the memory may also include a frame buffer for storing data arrays.

Each of the assessment system 120 and the user system 140 may include at least one processor 124 and 144, respectively. The at least one processor can be implemented as one or more integrated circuits (e.g., one or more single-core or multi-core microprocessors or microcontrollers) that can execute a variety of actions in response to corresponding instruction (e.g., program code).

In some embodiments, the assessment system 120 may include a number of executable modules or executable components (e.g., 128a and 130) and the user system 130 may include a number of executable modules or executable components (e.g., 148). As used herein, the term "executable module" or "executable component" can refer to software objects, routines, or methods that may be executed on the computing system. The different components, modules, engines, and services described herein may be implemented as objects or processes that execute on the computing system (e.g., as separate threads).

In some embodiments, the memory 122 can be used for storing a plurality of performance data 122a from a plurality of users with respect to one or more populations. The performance data may include context-specific eye movement data, such as eye movement data collected from a user during one or more testing or training phases (e.g., of users with respect to one or more collections of images), the one or more performance measures determined by the assessment system 120 using the eye movement data, the one or more other performance measures determined using other user-specific data (e.g., other behavioral, sensory and/or physiological data of that user), among others, or any combination thereof.

In some embodiments, the one or more performance measures may include one or more memory performance measures and/or one or more salience performance measures determined with respect to one or more images for a plurality of users of a population. The one or more memory performance measures and/or one or more salience performance measures for each user may be determined for a plurality of time ranges within the period of display for that image.

For example, the performance data 122a for each user may include the eye movement data (eye gaze coordinates defined by time) associated with the images presented collected for that user, one or more performance measures determined for that user, demographic and/or population information associated with that user, other physiological data associated with that user, among others, or a combination thereof.

The memory 122 may be used for a storing a plurality of test (parameter) data 122b. The test phase data may include one or more parameters for an assessment test to assess user(s) with respect to one or more populations. The one or more parameters may be specific to the test to be displayed, the analysis performed by the system 120 with respect to the images and/or measures, among others, or any combination thereof. For example, the one or more parameters may include the images of the first and/or the second collection to display, the display sequence (order of the images, period of time between images, the period of time between sessions, etc.), the analysis to be performed (e.g., the model generated by the model generator 128 and stored in the memory 122b), measure(s) to be determined, measure parameters/variables (e.g., bounding box size, analysis variables and/or location), among others, or a combination thereof. For example, he assessment(s) can be determined using measures determined with respect to time ranges within the display period of an image. The measures may be determined with respect to one or more different variables (e.g., other than time).

In some embodiments, the model generator 128 may be configured to generate one or more models for assessing an individual user and/or an image using the performance data 122a with respect to one or more populations/receive the performance data 122a. For example, the model generator may be configured to receive the performance data 122a for a particular set of variables and/or populations(s) to generate one or more models that maps/relates the performance data to a categorical, qualitative and/or quantitative assessment of a user and/or images.

In some embodiments, the model generator 128a may be operable to perform regression analysis on the performance data 122a to determine the test data 122b. In some embodiments, the model generator 128 may be configured to use machine learning techniques to correlate performance data to probability with respect to one or more populations in order to generate a predictive model that is operable to generate a probability of a user to be within one or more populations, as output, based on determined performance values. In some embodiments, the model generator 128 may be configured to use machine learning techniques to correlate performance data to a ranking of images with respect to one or more populations in order to generate a predictive model that is operable to generate a ranking of images to be desirable (e.g., salient) to one or more populations, as output, based on determined performance values.

In some embodiments, the user system 140 may include includes a user interface application ("UI application") 142b operable on the user system 140. The UI application 142b may be a visual application (e.g., video game, a virtual reality or augmented reality simulator), an audio or audio-visual service, or any other application capable of administering the test on a display (e.g., displaying images of the test at predetermined times), capable of determining and/or transmitting recorded eye movement data with respect to the display, among others, or any combination thereof.

In some embodiments, the assessment system 120 and the user system 140 can include other input/output hardware 126 and 146, including one or more keyboards, mouse controls, touch screens, microphones, speakers, display screens, track balls, and the like to enable the receiving of information from a user and for displaying or otherwise communicating information to a user.

In some embodiments, each of the assessment system 120 and the user system 140 may include one or more communication interfaces 130 and 148, respectively, configured to transmit and receive communications over network 110. One or more of communication interfaces 130 and 148 can include an antenna and supporting circuitry to support wireless data communication (e.g., using Bluetooth®, Bluetooth Low Energy, Wi-Fi, near-field communication or other wireless-communication protocol, etc.). It will be appreciated that different device/systems may communicate differently. For example, the acquisition devices 150 and the user system 140 may communicate over a Bluetooth® network, and the assessment system 120 and the user system 140 may communicate over a Wi-Fi network.

The various components illustrated in FIG. 1 represent only a few example implementations of a computer system for assessing an image and/or user. Other embodiments may divide the described memory/storage data, modules, components, and/or functions differently among the assessment system 120 and the user system 140, and some embodiments may move more of the processing toward the user system 140 than the assessment system 120, or vice versa, relative to the particular embodiment illustrated in FIG. 1. In some embodiments, memory components and/or program modules are distributed across a plurality of constituent computer systems in a distributed environment. In other embodiments, memory components and program modules are included in a single integrated computer system. Accordingly, the systems and methods described herein are not intended to be limited based on the particular location at which the described components are located and/or at which their functions are performed.

In the description that follows, embodiments are described with reference to acts that are performed by one or more computing systems. If such acts are implemented in software, one or more processors of the associated computing system that performs the act direct the operation of the computing system in response to having executed computer-executable instructions. For example, such computer-executable instructions may be embodied on one or more computer-readable media that form a computer program product. An example of such an operation involves the manipulation of data. The computer-executable instructions (and the manipulated data) may be stored in the memory 122 of the assessment system 120, the memory 142 of the user system 140, and/or in one or more separate computer system components (e.g., in a distributed computer system environment).

Figure 2:
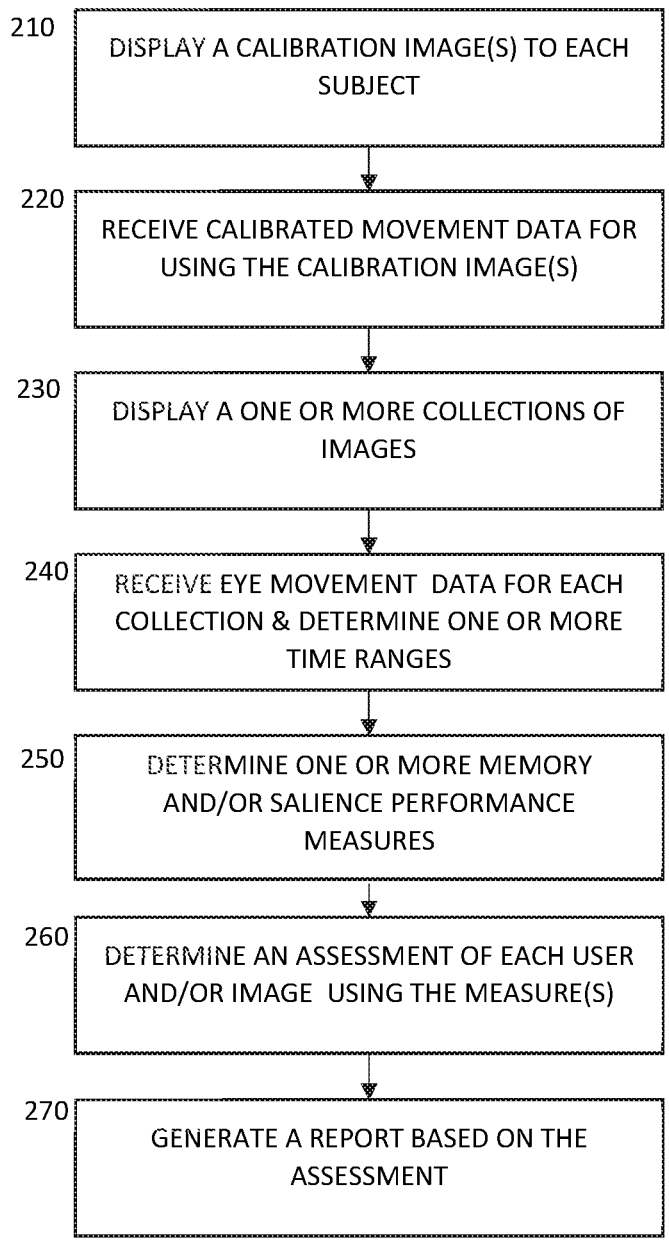
FIG. 2 shows a flowchart for a process of using at least eye movement data to determine a qualitative, quantitative, and/or categorical assessment of a user with respect to one or more populations, according to embodiments.
Figure 6:
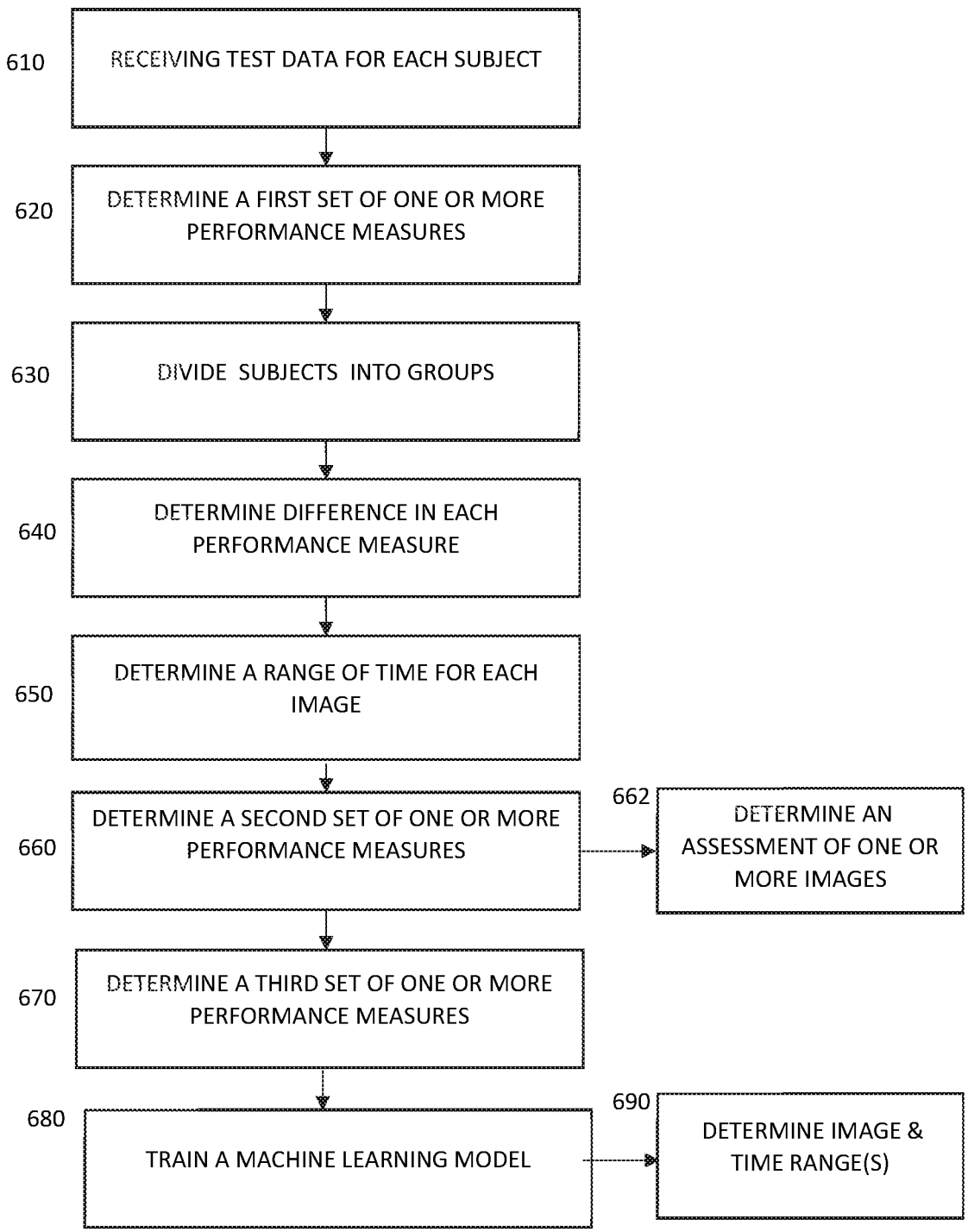
FIG. 6 shows a flowchart for a process of determining one or more parameters for an assessment test and/or process for determining a qualitative, quantitative, and/or categorical assessment of images presented to a population using at least eye movement data according to embodiments.
Figure 8:
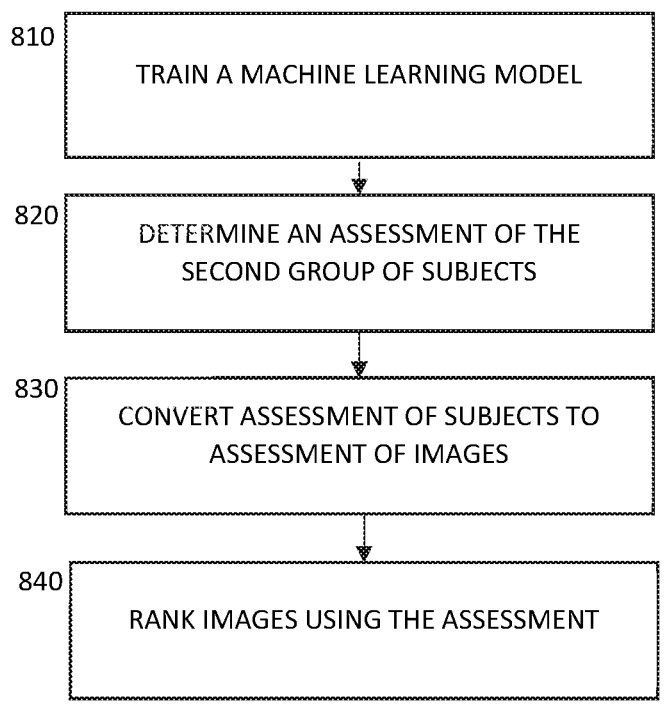
FIG. 8 shows a flowchart for a process of determining a qualitative, quantitative, and/or categorical assessment of images according to embodiments.

The computer-executable instructions may be used to implement and/or instantiate all of the functionality disclosed herein, including the functionality that is disclosed in reference to the flow diagram of FIGS. 2, 6, and 8.

FIG. 2 shows an exemplary method 200 of determining a quantitative, qualitative and/or categorical assessment of a user and/or image(s) according to embodiments. In some embodiments, the method 200 may start when a test for an individual assessment of a user, an assessment of one or more images, and/or for training the model is initiated.

In some embodiments, the method 200 may include a step 210 of displaying one or more images on a display screen to calibrate the eye movement data of the user. By way of example, the calibration image may include one or more visual targets. By way of example, the visual target be any item (e.g., part or whole of an image) for drawing a user's gaze. For example, the visual target may include a shape (e.g., circle, star, box, etc.), object (e.g., dot, cross, icon, etc.), among others, or any combination thereof.

Next, the method 200 may include a step 220 of receiving and calibrating the eye movement data. For example, the eye movement data may be measured by an eye tracking system (e.g., acquisition device 150) and transmitted to the system 120 and/or the system 140 for calibrating the eye movement data. The eye movement data may be calibrated using any known methods. It will also be understood that the method 200 may include additional and/or alternative steps to calibrate the eye movement data used in the one or more training sessions. By calibrating the eye movement data, a more accurate mapping from eye position to display location may be achieved thereby providing a more accurate determination of eye movement data of a user, e.g., user's gaze direction or fixation location on a display screen.

In other examples, the calibration phase (steps 210 and/or 220) may be performed by the acquisition device 150. For example, the calibration may be performed by the acquisition device so that the testing data transmitted to the assessment system 110 may be calibrated data and steps 210 and/or 220 may be omitted.

In some embodiments, after the calibration phase, the method 200 may initiate the one or more test sessions. The method 200 may include a step 230 of displaying one or more images from one or more collections for each test session on a display screen to the user.

In some embodiments, the one or more collections may include a first collection of one or more images. Each image of the first collection may be a different image. Each image of the first collection may include one or more regions (e.g., part of the image) that include and/or represent a visual target. The visual target may include but is not limited to an item, that is completely or partially visible (e.g., blurred), an area next to an item (e.g., landscape or scenery next to a bike), among others, or a combination thereof. The images of the first collection may be considered to be "reference images" or "original images."

In some embodiments, the one or more collections of images may include a second collection of images. Each image of the second collection may be modified versions of the corresponding image of the first collection (e.g., sequentially). For example, like the first image, each image of the second collection may include one or more regions (e.g., part of the image) that include and/or represent a visual target. One or more regions of the images of the second collection may be modified versions of the one or more regions of the corresponding images of the first collection. For example, one or more regions of the images of the second collection may omit one or more item, include a different item, blur an item, among others, or a combination thereof, as compared to the item(s) shown in the corresponding image of the first collection.

For example, the images of the first collection and/or the second collection may be displayed during one or more test sessions. The images of the first collection and/or the second collection may be still (e.g., static) and/or dynamic (e.g., video and/or interactive) images. In some embodiments, a session may include one or more images from the first collection, one or more images from the second collection, and/or a combination thereof. The images from the first collection should be displayed in a session before the corresponding images from the second collection. The one or more images from the first and/or second collection may be displayed in any order (e.g., in series, randomly, etc.) and do not need to be displayed in the same series with respect to sessions (e.g., the images from the first collection displayed during a first session and the corresponding images from the second collection displayed during a second session) and/or a within session (e.g. the images of the second collection are displayed in the same order as the corresponding images of the first collection). In some examples, the images from the first collection and/or the second collection may be displayed in a session in any order. For example, the images of the second collection can be displayed in a different order than the images of the first collection.

Each image may be displayed for a period of time within a session. The time that the image is displayed may be the same or different for each session, image, among others, or any combination thereof. The time between the display of images within a session and between sessions may the same or different for attest. There may be a delay between sessions. By way of example, a test may include a first session in which two images from the first collection is displayed for a period of time in the morning and a second session in which an image from the second collection, corresponding to one of the two images, is displayed for a period of time in the evening. In other embodiments, each image may be displayed for different amount of time. The test may also include any number of sessions.

The method 200 may include a step 240 of receiving eye movement data for each image of each test session/collection displayed, for example, from an acquisition device 150. The eye movement data may be spatiotemporal data. For example, the eye movement data may include and is not limited to eye gaze location (e.g., coordinates with respect to the display screen) defined by time.

The step 240 may include determining or separating the eye movement data for each time period for each image into a plurality of time ranges. The plurality of time ranges may be discrete (e.g., 0-1 sec, 1-2 sec, 2-4 sec, etc.), overlapping, or a combination thereof. For example, one or more of the time ranges may overlap the first time range. By way of example, for an image that was displayed for 5 seconds, the data may be separated into the following time bins: 0-1 sec, 0-2 sec, 0-3 sec, 0-4 sec, and 0-5 seconds. The plurality of time ranges may be predefined. The plurality of time ranges may be the same for each image.

Next, the method 200 may include a step 250 of determining one or more memory performance measures, one or more salience performance measures, among others, or a combination thereof. The step 250 may include determining one or more performance measures for one or more images of the first collection and/or the second collection displayed during the test session(s), for example, based on the parameters associated with the assessment stored in the memory 122. The one or more performance measures may be determined for one or more images using the eye movement data for a predetermined time range (e.g., one of the ranges from step 240). For example, the system may store the predetermined time range for each image for which the eye movement data and the respective image that should be used to determine the specific performance measure(s) for that image.

In some embodiments, the one or more memory performance measures may be determined for one or more images of the second collection using the eye movement data for those images. In some embodiments, the step 250 may include only determining one or more memory performance measures.

In some embodiments, the step 250 may also include determining one or more salience performance measures. In some embodiments, the one or more salience performance measures may be determined for one or more images of the first collection using the eye movement data of those images. In some embodiments, the step 250 may also include determining alternative or additional performance measures.

In some embodiments, the one or more memory performance measures for each image may be determined using gaze location data for the one or more regions of one or more images of the second collection for one or more time ranges. For example, the one or more memory performance measures may be determined using a gaussian function, a bounding box, among others, or any combination thereof.

For example, the one or more memory performance measures may include a first memory performance measure. The first memory performance measure may be determined for a one or more images of the second collection by constructing a gaussian function wherein the mean of the gaussian may approximately lie around the center of each region while the variance may correspond to the edges of that region using the eye movement data (e.g., eye gaze data) for the predetermined time range for that image. The outputs of the gaussian function can then be averaged to generate the first memory performance measure. The greater the first memory performance measure, the greater the memory for that region. This way, the step 250 may determine at least a first memory performance measure for one or more images of the second collection using the eye movement data for the predetermined time range for that image and measure.

In another example, the one or more performance measures may additionally or alternatively include a second memory performance measure for one or more images of the second collection. The second memory performance measure may be determined by constructing a bounding box so that the center of the bounding box corresponds to the center of the region. By way of example, the bounding box may be an ellipse. In this example, the ellipse may be constructed so that the center of the ellipse lies around the center of the region and the major axis and minor axis are positioned to correspond to the edges of the region. It will be understood that a different shape of a bounding box may be used, including, but not limited to a circle, square, among others, or any combination thereof. The second memory performance measure may correspond to the percentage of all gaze positions that are within the bounding box of the region for the predetermined time range(s). The second memory performance measure can indicate the amount of time that was spent viewing the region of each image. The greater the relative viewing time within the region of an image of the second collection, the greater the memory (e.g., removed or added object) for that region with respect to the corresponding image of the first collection.

In some embodiments, the first memory performance measure and/or the second memory performance measure may be determined for each image of the second collection. In other embodiments, the first memory performance measure and/or the second memory performance measure may be determined for a subset of one or more images of the second collection. In some embodiments, the subset for the first memory performance measure and the subset for the second memory performance measure may include the same images and/or different images.

In some embodiments, the one or more performance measures may additionally or alternatively include one or more salience performance measures. For example, the one or more salience performance measures may include a first salience performance measure. The first salience performance measure may be determined for one or more images of the first collection by constructing a gaussian function wherein the mean of the gaussian may approximately lie around the center of each region while the variance may correspond to the edges of that region for an image of the second collection. The outputs of the gaussian function can then be averaged to generate the first salience performance measure. The greater the first salience performance measure for a region of an image, the greater the salience for that region/image. This way, the step 250 may determine at least a first salience performance measure for one or more images of the first collection using the eye movement data for the predetermined time range for that image and measure.

In another example, the one or more performance measures may additionally or alternatively include a second salience performance measure for one or more image of the first collection. The second salience performance measure may be determined by constructing a bounding box to cover at least a portion of the region. In some embodiments, the bounding box may be constructed so that the center of the bounding box corresponds to the center of the region. By way of example, the bounding box may be an ellipse. In this example, the ellipse may be constructed so that the center of the ellipse lies around the center of the region and the major axis and minor axis are positioned to correspond to the edges of the region. It will be understood that a different shape of a bounding box may be used, including, but not limited to a circle, square, among others, or any combination thereof. The second salience performance measure for an image may correspond to the percentage of all gaze positions that are within the bounding box of the region for the predetermined time range(s). The second salience performance measure can indicate the amount of time that was spent viewing the region of each image. The greater the relative viewing time within the region of an image of the first collection, the greater the salience (e.g., removed or added object) for that region.

In some embodiments, the first salience performance measure and/or the second salience performance measure may be determined for each image of the first collection. In other embodiments, the first salience performance measure and/or the second salience performance measure may be determined for a subset of one or more images of the first collection. In some embodiments, the subset for the first salience performance measure and the subset for the second salience performance measure may include the same images and/or different images.

Next, the method 200 may include a step 260 of determining a quantitative, qualitative and/or categorical assessment of a user and/or image(s) using the one or more performance measures. In some embodiments, the assessment may include an assessment for each performance measure determined. In other embodiments, the assessment may include one assessment for one or more performance measures determined.

In some embodiments, the assessment may include one or more of a score, rank, probability, a category, among others, or a combination thereof. For example, for a user, the assessment may include one or more numerical values (i.e., percentage) representing the probability that a user belongs to a population category (e.g., healthy vs. cognitive disorder; young vs. old; etc.).

In some embodiments, the step 260 may include determining an assessment for each performance measure for the user. By way of example, if the step 240 determined the first and second memory performance measures, then the step 260 may determine two assessments. In other embodiments, the step 260 may determine an assessment using at least the performance measures determined in step 250.

The assessment may be determined by applying machine learning and/or regression techniques to the one or more performance measures. In some embodiments, the assessment may use one or more classifiers that are based upon training data set(s) of statistically representative performance measures determined using statistically representative eye movement data of representative populations. In some embodiments, the method may include utilizing the classifiers to determine and/or compute the assessment of the performance measures.

For example, the step 260 may include transforming the one or more memory performance measures into an assessment by using a trained logistic regression model, for example, stored in the memory 122. The logistic regression model may be trained using the one or more memory performance measures of a plurality of users of the population(s) to be assessed. For example, when the method 200 is used as a screening tool for memory loss including clinically defined mild cognitive impairment or Alzheimer's disease, the logistic regression model may be trained, for example, as described in Figure X, using eye movement data collected during the test from healthy users and users diagnosed with Alzheimer's disease. The one or more memory performance measures determined (e.g., in step 250) for a user to be assessed using one or more of the images that trained the model for a user may be inputted into the trained logistic regression model to determine the assessment. In this example, the assessment may result in a probability of having clinical mild cognitive impairment or Alzheimer's Disease. The probability may represent a personalized severity score of the user. This way, the assessment (probability/personalized severity score) may allow the clinician and the user/family/caregiver to track deterioration or improvement, and to aid decision support concerning therapy, living/caregiving environment choices, or use of assistive technologies. For example, the assessment (probability/personalized severity score) can be tracked for several tests over a period of time.

In some embodiments, the assessment may additionally and/or optionally include transforming the one or more salience performance measures into an assessment by using a trained logistic regression model, for example, stored in the memory 122. The logistic regression model may be trained using the one or more salience performance measures of a plurality of users of the population(s) to be assessed.

In some embodiments, the assessment of the one or more performance measures may be determined using additional and/or alternative machine learning and/or regression techniques (e.g., linear regression).

In some embodiments, the step 260 may optionally (alternatively and/or additionally) include determining an assessment of each image of the first collection and/or the collection using the one or more performance measures for one or more subjects. The assessment may include ranking the images based on salience and/or memory performance measures.

For example, an advertiser desires 100 images to be evaluated for a specific time range (0-5 seconds). In this example, the one or more performance measures may be determined for each image at that specific time for one or more subjects. Using these measures, the images may be ranked highest to lowest value with respect with the measure type. For example, for each measure, a ranked list may be generated. The highest value is more salient or memorable than the lower value. If more measures for more than one subject is used, than the averaged measures for each image may be used to generate measure of memory and/or salience for a specific population.

Next, the method 200 may optionally include a step 270 of generating a report based on the assessment. For example, the report may be for the user, the clinician and/or customer (e.g., advertiser). For example, the report may include but is not limited to the details the results of the assessment, provide a tracking of the user's progress (e.g., if being monitored over several test sessions), graphical visualizations, among others, or a combination thereof.

In some embodiments, the method 200 may additionally or optionally include storing the assessment, updating one or more models with the assessment, among others, or any combination thereof.

Figure 3:
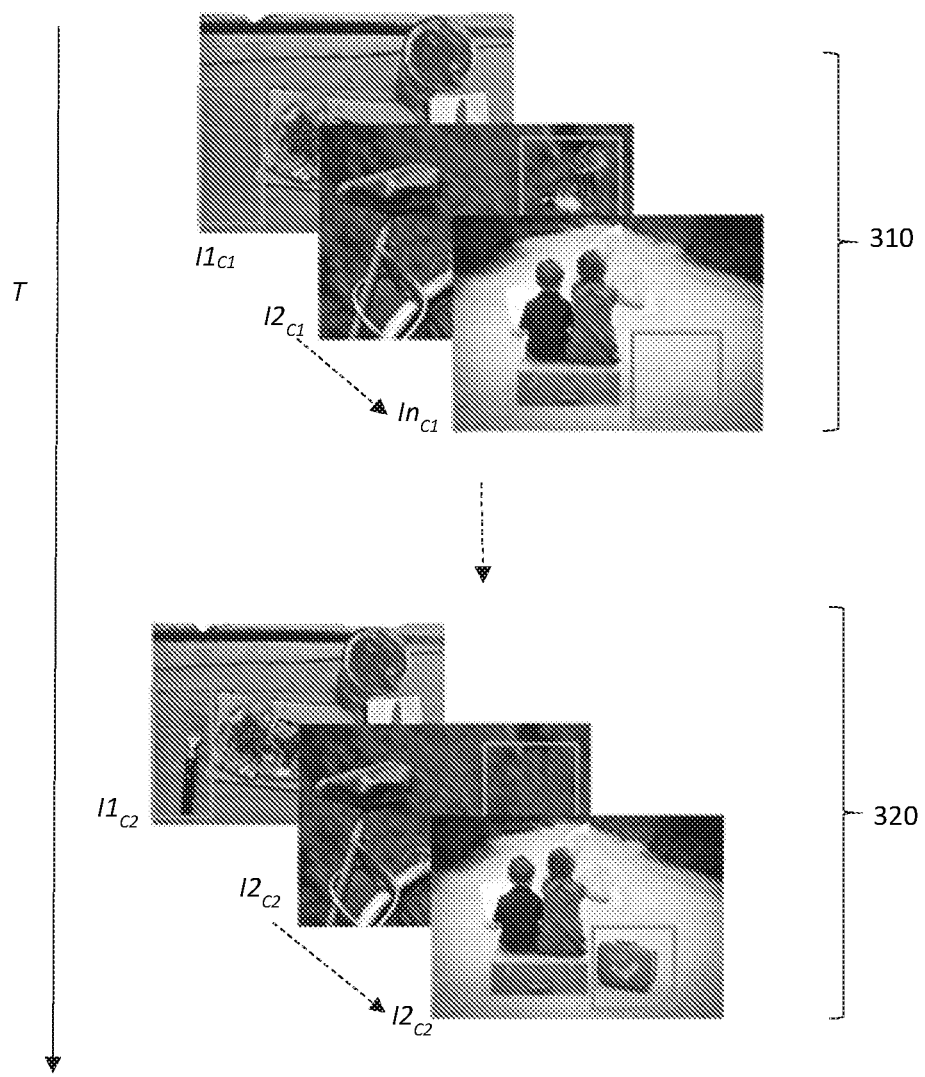
FIG. 3 shows an example of a test presented to a user according to embodiments.

FIG. 3 shows an example 300 of a test, for example, that can be displayed on a display screen in steps 230, for assessing a user and/or images according to embodiments. In this example, the calibration is performed by the eye movement acquisition device so the eye movement data received is calibrated eye movement data. The test may include a display of one or more images from a, first collection 310 of images ($I1_{CI}$ ... $In_{CI}$) in one or more test sessions. The images of the first collection 310 may be considered the reference or original images. The test may include a display of one or more images from a second collection 320 of images ($I1_{C2}$ ... $In_{C1}$) on the display screen in one or more test sessions. The images of the second collection 320 may be modified versions of the reference or original images of the first collection 310. By way of example, image $I1_{C2}$ from the second collection 320 may be a modified version of image $I1_{C1}$ from the first collection 310, image $I2_{C2}$ from the second collection 320 may be a modified version of the image $I2_{C1}$ from the first collection 310, and image $In_{C2}$ from the second collection 320 may be a modified version of the image $In_{C1}$ from the first collection 310.

If the test includes one or more images from the second collection 320, the corresponding original reference from the first collection 310 should be displayed before the corresponding image of the second collection in the same and/or different session. In some examples, the original/reference image(s) of the first collection 310 and the corresponding modified image(s) of the second collection 320 may be shown in the same order in one or more sessions. By way of example, if the test includes displaying the collections consecutively in one session, the total time (T) for the test 300 for a user to perform the test may be within a few minutes (e.g., 3-5 min). This way, memory and/or salience may be more efficiently and accurately accessed without distressing or frustrating the user and using less resources.

In some examples, one or more images from the first and/or second collections may be displayed over a plurality of sessions that are separated by significant an amount of time (e.g., not in one sitting). For example, the displaying of the images and/or initiating of the test session(s) may be separated by over 10 minutes, hour(s), day(s), etc. so that the memory change of a user may be tracked longitudinally with respect to the user and/or population(s).

The number of images for each collection may include any number of images and is not limited to the three. The images shown in the first and/or second collection may be different.

Figure 4:
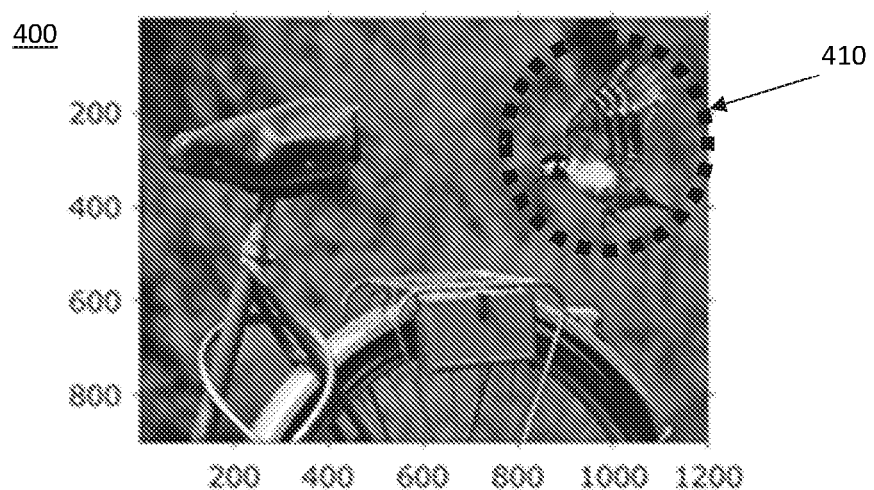
FIG. 4 shows an example of images from a first collection according to embodiments.
Figure 5:
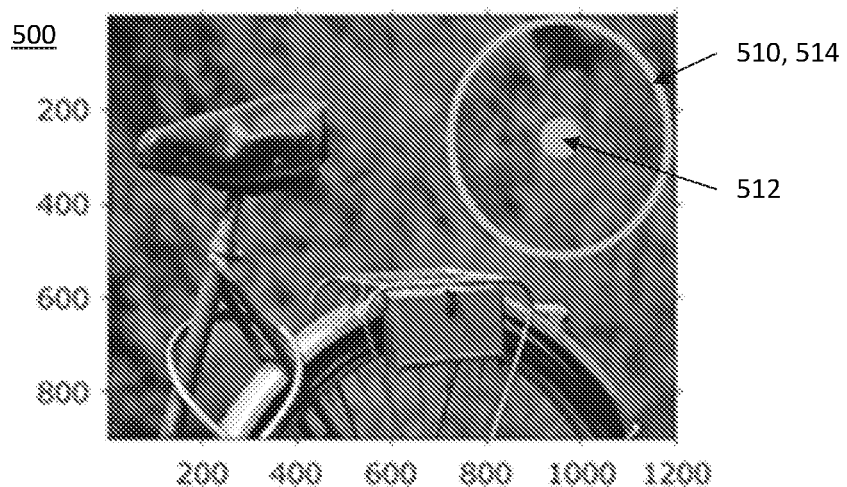
FIG. 5 shows an example of images from a second collection corresponding to the image of the first collection according to embodiments.

FIG. 4 shows an enlarged version 400 of the image $I1_{C1}$ of the first testing phase 320 with respect to the coordinate system and FIG. 5 shows an enlarged version 500 of the corresponding modified image $I1_{C2}$ of the second testing phase 330 with respect to the coordinate system. In this example, the bird displayed in region 410 of the image 400 can corresponds to the region for which the one or more salience performance measures may be determined using the eye movement data for the predetermined time range. In FIG. 5, the region 510 of the image 500 corresponds to the region 410. As shown in this example, the image 500 is different from the image 400 because the bird has been removed from the region 510. By way of example, the one or more memory performance measures may be determined using the eye movement data with respect to the region 510. For example, the second memory performance measure may be determined using the bounding box (e.g., an elliptical) 514 that corresponds to the region 510 having a center 512 of the region.

FIG. 6 shows a method 600 of training a classifier that can be used to perform a quantitative, qualitative and/or categorical assessment of one or more users and/or a method for determining a quantitative, qualitative and/or categorical assessment of one or more images, and determining one or more parameters for the test, according to embodiments. The one or more parameters may include the predetermined time range to process the eye movement data, size and/or shape of bounding box, the period of time to display an image, the images to be included in the first collection and/or the second collection, order of the images to be displayed, the period of time between the display images, the assessment to be performed (e.g., the variables (e.g., time range) to which the measures may be determined), among others, or a combination thereof.

In some embodiments, the method may include a step 610 of receiving test data for a plurality of users. The test data may include eye movement data for each image of the testing phase for the period of time for each user. For example, the step 610 may include administering a test, for example, as shown in FIG. 3, to each of the plurality of users by detecting eye movement data while displaying the test on a display screen. The method may include steps 210-230 shown and described with respect to method 200.

In some embodiments, the method 600 may include a step 620 of determining a first set of one or more performance measures for each user for each time range of the time period. The first set of one or more performance measures may include but is not limited to one or more memory performance measures, one or more salience performance measures, among others, or a combination thereof. For example, the one or more performance measures may include a first memory performance measure, a second memory performance measure, a first saliency performance measure, and/or a second salience performance measure. Similar to step 250 of FIG. 2, the step 620 may determine the one or more memory and/or salience performance measures for each image using gaze location data for the one or more regions of each image of the respective test session for each time ranges. For example, the one or more memory and/or salience performance measures may be determined using a gaussian function, bounding box, among others, or any combination thereof.

For example, the first memory performance measure and the first salience performance measure may be determined of each image of the second collection and each image of the first collection, respectively, by constructing a gaussian function wherein the mean of the gaussian may approximately lie around the center of each region while the variance may correspond to the edges of that region using the eye movement data (e.g., eye gaze data) for each time range of the period of time. The second memory performance measure and the second salience performance measure may be determined of each image of the second collection and each image of the first collection, respectively, by constructing a bounding box on the respective image so that the center of the bounding box (e.g., ellipse) corresponds to the center of the region. The outputs of the gaussian function may then be averaged to determine the first memory performance measure and the first salience performance measure.

Next, the method 630 may include dividing the users and associated performance measure(s) into two or more groups. For example, the users and associated performance measure(s) may be divided into a first group and a second group. The first group may be used as a training group and the second group may be used as a testing group.

In some embodiments, the first group may be further divided into one or more subgroups according to population(s) to be evaluated. For example, if training the model to assess a cognitive disorder, the first group may be divided into a first subgroup (e.g., healthy controls) and a second subgroup (e.g., symptomatic Alzheimer's disease, cognitively impaired individuals, etc.). For example, the subgroups may be determined using available medical data of the user including but not limited to brain imaging, bloodwork, previous diagnosis, neurological exam, standardized neurophysical testing, other assessments (e.g., Montreal Cognitive Assessment (MoCA), among others, or any combination thereof. If the model is being trained to assess memory relative to age, the first group may be divided based on age into a first subgroup (e.g., young users) and a second subgroup that are older than the first subgroup.

The method 600 may include a step 640 of determining a difference in the first set of performance measures between the subgroups for each time range for each image. For example, the differences between the subgroups may be determined for the associated first memory performance measure, the second memory performance measure, the first salience performance measure, and/or the second salience performance measure, among others, or any combination thereof.

The method 600 may include a step 650 of determining the time range of each period of time for each image that has the maximum difference in performance measures determined in step 640 between the two subgroups.

Figure 7:
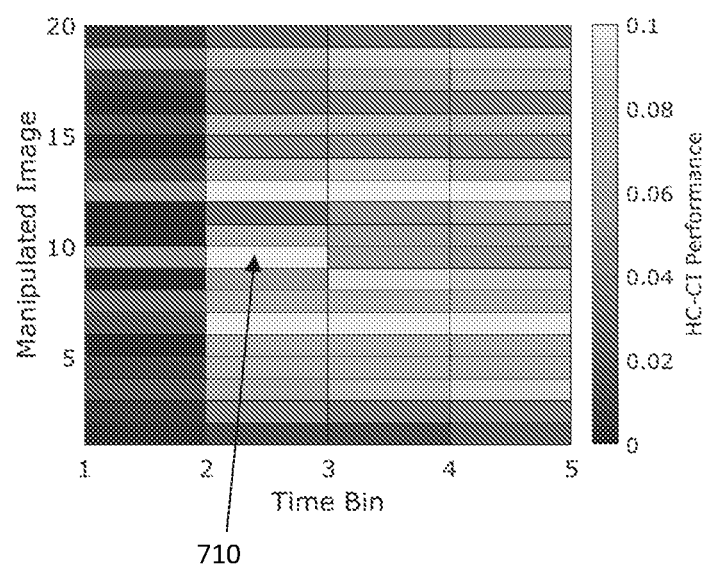
FIG. 7 shows an example of an illustration of the determination of the third set of performance values according to embodiments.

FIG. 7 shows an example 700 of a spectrogram representing the difference between two subgroups for the first memory performance measure: healthy controls and cognitive impaired users for a specific image and a specific time bin. In this example, each subgroup has 50 healthy controls and 50 AD patients. For each time range for each image, the first memory performance measure may be averaged for each subgroup and then the difference between the averaged measures of the subgroups may be determined. In this example, the lighter the bin in this figure the bigger the difference. In this example, for image 9, the maximum difference is time range (or time bin) 3 identified by 710. This time range 710 has a difference of about 10%.

Next, the method 600 may include a step 660 of determining a second set of performance measures for each user (of both groups) for each image for the time range determined in step 650. For example, a second set of performance measures may include the first memory performance measure, the second memory performance measure, the first salience performance measure, and/or the second salience performance measure. For the images of the second collection, the step 660 may include determining a first memory performance measure and a second memory performance measure for each image for the time range determined in step 650. For the images of the first collection, the step 660 may include determining a first salience performance measure and a second salience performance measure for each image for the time range determined in step 650.

In some embodiments, the method 600 may include a step 670 of determining a third set of performance measures for each user, for example, using the second set of performance measures (determined in step 660) and the difference in each performance measure at (determined in step 620). The third set of performances may be determining by iteratively averaging the performance measure for one or more time ranges based on associated ranking with respect to the difference.

By way of example, each user may have a second set of 20 first memory performance values. Each first memory performance value of the second set corresponds to the memory performance value for time range determined in step 650. Using the differences determined in step 650 (e.g., FIG. 7), the measures with the highest difference are ranked. Using the ranking, the third set of memory performance values may correspond to the iterative average of the measures based on the rankings. This way, the third set of memory performance values can correspond to an aggregate of multiple images presented.

By way of example, using the differences shown in FIG. 7, the ranking of the top 3 second set of first memory measures would be the values associated with measures for images 6, 9, and 12. In this example, for that user, the third set of performance values would include a first performance value that corresponds to the second set of first memory measure for image 6; a second performance value that corresponds to the average of second set of first memory measures for images 6 and 9; and a third performance value that corresponds to the average of the second set of first memory measures for images 6, 9, and 12. In this example, the step 670 would generate a third set of 20 first memory performance values.

In some embodiments, the method 600 may include a step 680 processing the third set of one or more performance measures (step 670) to determine one or more variables for the machine learning model. For example, if the machine learning model utilizes logistic regression, the step 680 may include determining one or more parameters using these measures using backpropagation. In some embodiments, other methods may be used.

The method 600 may include a step 690 of determining one or more parameters for one or more test sessions. For example, the step 690 may include determining one or more images from the first collection and associated predetermined/reference time range for assessing a user for when using the model (step 670). In some embodiments, the step 690 may include determining assessment of each user of the second (e.g., control) group using the model trained in step 680 and the measures determined in step 650. By way of example, the assessment may include a probability that a testing user is within one of the two subgroups of the first group (e.g., young vs. old, cognitive impaired vs. healthy, etc.).

The step 690 may include converting the probabilities into a representation or reflection of sensitivity and specificity to determine a set of the reference images for the first collection and associated predetermined time range for performing an assessment. For example, the step 690 may include. converting the third set of performance values into an area under curve (AUC) and ranking the AUCs from highest to lowest. By way of example, if the $8^{th}$ performance value within the third set is highest, then the eight images and associated reference time ranges may be selected for a test to assess a probability of a user having Alzheimer's disease. This way, step 690 can determine test session data (e.g., one or more parameters for a test).

The method 600 may include storing and/or transmitting the model and the reference time range and associated image, for example, for use in step 260.

In some embodiments, if the method 600 is being used to determine an assessment of one or more images that are displayed during the testing phase(s), the method 600 may optionally include a step 662 for determining an assessment of one or more images presented during the test. FIG. 8 shows an example of a method 800 of determining an assessment of one or more images using the second set of performance measures determined in step 650.

In some embodiments, the method 800 may include a step 810 of processing the second set of memory and/or performance measures for the first group to train a machine learning model. For example, if the machine learning model utilizes logistic regression, the 662 may include determining one or more variables using these measures using back-propagation. In some embodiments, other methods may be used.

The method 800 may include a step 820 of determining assessment of each user of the second group using the model trained in step 810 and the measured determined in step 650. By way of example, the assessment may include a probability that a testing user is within one of the two subgroups of the first group (e.g., young vs. old, cognitive impaired vs. healthy, etc.).

The method 830 may include a step 830 may include converting the assessment of the user to an assessment of the image by converting the probabilities into a representation or reflection of sensitivity and specificity, such as converting the probabilities into an area under curve.

Next, the method 800 may include a step 840 of ranking the images from the first and/or second collections using the assessments of the images (step 830). The images that are ranked highest may be those that best separate two populations. In some embodiments, the test may be modified to include these images and the associated time ranges for calculating the assessment of the user. The ranking of the images may also be provided within a report (e.g., step 270). The images ranked higher can maximize the difference in salience between the first group and the second group. For example, the ranking can provide identify images that maximize the difference in salience and/or memorability between the older population and overall population, which can be used for product advertisement. For example, if training a model for assessing Alzheimer's Disease, the ranking of the images of the first collection can correspond to ranking of images separating Alzheimer's Disease with respect to salience and the ranking of the images of the second collection can correspond to ranking of images separating Alzheimer's Disease with respect to salience.

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other embodiments, well-known circuits, processes, algorithms, structures, and techniques can be shown without unnecessary detail in order to avoid obscuring the embodiments.

Implementation of the techniques, blocks, steps and means described above can be done in various ways. For example, these techniques, blocks, steps and means can be implemented in hardware, software, or a combination thereof. For a hardware implementation, the processing units can be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above, and/or a combination thereof.

Also, it is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed but could have additional steps not included in the figure. A process can correspond to a method, a function, a procedure, a subroutine, a subprogram, etc. When a process corresponds to a function, its termination corresponds to a return of the function to the calling function or the main function.

Furthermore, embodiments can be implemented by hardware, software, scripting languages, firmware, middleware, microcode, hardware description languages, and/or any combination thereof. When implemented in software, firmware, middleware, scripting language, and/or microcode, the program code or code segments to perform the necessary tasks can be stored in a machine readable medium such as a storage medium. A code segment or machine-executable instruction can represent a procedure, a function, a subprogram, a program, a routine, a subroutine, a module, a software package, a script, a class, or any combination of instructions, data structures, and/or program statements. A code segment can be coupled to another code segment or a hardware circuit by passing and/or receiving information, data, arguments, parameters, and/or memory contents. Information, arguments, parameters, data, etc. can be passed, forwarded, or transmitted via any suitable means including memory sharing, message passing, ticket passing, network transmission, etc.

For a firmware and/or software implementation, the methodologies can be implemented with modules (e.g., procedures, functions, and so on) that perform the functions described herein. Any machine-readable medium tangibly embodying instructions can be used in implementing the methodologies described herein. For example, software codes can be stored in a memory. Memory can be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium", "storage" or "memory" can represent one or more memories for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes but is not limited to portable or fixed storage devices, optical storage devices, wireless channels, and/or various other storage mediums capable of storing that contain or carry instruction(s) and/or data.

While the disclosure has been described in detail with reference to exemplary embodiments, those skilled in the art will appreciate that various modifications and substitutions may be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed:

1. A method for determining a qualitative, quantitative and/or categorical assessment of one or more users and/or images with respect to one or more populations, comprising:
presenting a test to a user on a display screen of a computing device, the test including displaying a plurality of images comprising a first image from a first collection and a second image from a second collection for a period of time, wherein the first image comprises a plurality of regions and the second image comprises the same plurality of regions with one modified region of the plurality of regions;
obtaining eye movement data of the user with respect to the first and the second images displayed, the eye movement data for each image including eye gaze position data for the period of time;
determining one or more memory performance measures and/or one or more salience performance measures using the eye movement data with respect to the modified region of the second image for one or more of predetermined time ranges of the period of time; and
determining a quantitative, qualitative and/or categorical assessment of the user with respect to one or more populations, using the one or more memory performance measures and/or one or more salience performance measures.

2. The method according to claim 1, the method further comprising:
detecting eye movement of the user with respect to each image displayed on the display screen for the period of time.

3. The method according to claim 1, wherein:
the test includes one or more first images of the first collection;
the first collection of images including one or more reference images; and
each reference image of the first collection of images is displayed for the period of time.

4. The method according to claim 1, wherein:
the test includes one or more second images of the second collection;
each image of the second collection corresponding to an image of the first collection;
each image of the second collection having one region that is different from one region of the corresponding image of the first collection; and
each image of the second collection is displayed for the period of time.

5. The method of claim 4, wherein:
the images of the second collection are displayed after the images of the first collection.

6. The method of claim 1, wherein the determining one or more memory performance measures and/or one or more salience performance measures includes determining one or more memory performance measures, the one or more performances measures being determined based on the performance measures for the second collection of images.

7. The method of claim 1, wherein the determining one or more memory performance measures and/or one or more salience performance measures includes determining one or more salience performance measures, the one or more salience performances measures being determined based on the performance measures for the first collection of images.

8. The method of claim 1, wherein the one or more populations includes individuals diagnosed with Alzheimer's Disease.

9. A system for determining a qualitative, quantitative and/or categorical assessment of one or more users and/or images with respect to one or more populations, comprising:
one or more processors; and
one or more hardware storage devices having stored thereon computer-executable instructions which are executable by the one or more processors to cause the computing system to perform at least the following:
presenting a test to a user on a display screen of a computing device, the test including displaying a plurality of images comprising one or more imaes a first image from a first collection and a second image from a second collection for a period of time, wherein the first image comprises a plurality of regions and the second image comprises the same plurality of regions with one modified region of the plurality of regions;
obtaining eye movement data of the user with respect to the first and the second images displayed, the eye movement data for each image including eye gaze position data for the period of time;
determining one or more memory performance measures and/or one or more salience performance measures using the eye movement data with respect to the modified region of the second image one or more images for one or more of predetermined time ranges of the period of time; and
determining a quantitative, qualitative and/or categorical assessment of the user with respect to one or more populations, using the one or more memory performance measures and/or one or more salience performance measures.

10. The system according to claim 9, wherein the one or more processors are further configured to cause the computing system to perform at least the following:
detecting eye movement of the user with respect to each image displayed on the display screen for the period of time.

11. The system according to claim 9, wherein:
the test includes one or more first images of the first collection;
the first collection of images including one or more reference images; and
each reference image of the first collection of images is displayed for the period of time.

12. The system according to claim 9, wherein:
the test includes one or more second images of the second collection;
each image of the second collection corresponding to an image of the first collection;
each image of the second collection having one region that is different from one region of the corresponding image of the first collection; and
each image of the second collection is displayed for the period of time.

13. The system of claim 12, wherein:
the images of the second collection are displayed after the images of the first collection.

14. The system of claim 9, wherein the determining one or more memory performance measures and/or one or more salience performance measures includes determining one or more memory performance measures, the one or more performances measures being determined based on the performance measures for the second collection of images.

15. The system of claim 9, wherein the determining one or more memory performance measures and/or one or more salience performance measures includes determining one or more salience performance measures, the one or more salience performances measures being determined based on the performance measures for the first collection of images.

16. The system of claim 9, wherein the one or more populations includes individuals diagnosed with Alzheimer's Disease.

* * * * *